US010107826B2

(12) United States Patent
Yoshimura et al.

(10) Patent No.: US 10,107,826 B2
(45) Date of Patent: Oct. 23, 2018

(54) IMMUNOASSAY METHODS AND REAGENTS FOR DECREASING NONSPECIFIC BINDING

(75) Inventors: Toru Yoshimura, Chiba (JP); Eisaku Yoshida, Chiba (JP); Ryotaro Chiba, Chiba (JP)

(73) Assignee: Abbott Japan Co. Ltd., Chiba-Ken (JP)

( * ) Notice: Subject to any disclaimer, the term of this patent is extended or adjusted under 35 U.S.C. 154(b) by 0 days.

(21) Appl. No.: 13/472,683

(22) Filed: May 16, 2012

(65) Prior Publication Data

US 2013/0130275 A1 May 23, 2013

Related U.S. Application Data

(60) Provisional application No. 61/488,421, filed on May 20, 2011.

(51) Int. Cl.
G01N 33/86 (2006.01)

(52) U.S. Cl.
CPC .................. *G01N 33/86* (2013.01)

(58) Field of Classification Search
CPC ...................................... G01N 33/86
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,780,410 A * | 10/1988 | Matsuda et al. | 435/7.4 |
| 4,956,778 A | 9/1990 | Naito | |
| 5,006,309 A | 4/1991 | Khalil et al. | |
| 5,063,081 A | 11/1991 | Cozzette et al. | |
| 5,089,424 A | 2/1992 | Khalil et al. | |
| 5,091,513 A | 2/1992 | Huston et al. | |
| 5,104,621 A * | 4/1992 | Pfost et al. | 422/67 |
| 5,132,405 A | 7/1992 | Huston et al. | |
| 5,156,950 A * | 10/1992 | Akino et al. | 435/7.5 |
| 5,247,067 A * | 9/1993 | Arima et al. | 530/324 |
| 5,252,712 A | 10/1993 | Furie et al. | |
| 5,470,711 A * | 11/1995 | Bean et al. | 435/7.1 |
| 5,543,524 A | 8/1996 | Mattingly et al. | |
| 5,565,570 A | 10/1996 | Mattingly et al. | |
| 5,783,699 A | 7/1998 | Mattingly et al. | |
| 6,342,220 B1 * | 1/2002 | Adams | C40B 40/02 424/133.1 |
| 6,887,714 B2 | 5/2005 | Fritsch et al. | |
| 6,893,831 B1 * | 5/2005 | Kanashima et al. | 435/7.94 |
| 7,303,884 B1 * | 12/2007 | Bertling | G01N 33/86 435/7.1 |
| 7,635,571 B2 * | 12/2009 | Ullman et al. | 435/7.94 |
| 2003/0170881 A1 | 9/2003 | Davis et al. | |
| 2004/0018577 A1 | 1/2004 | Emerson Campbell et al. | |
| 2005/0054078 A1 | 3/2005 | Miller et al. | |
| 2006/0099567 A1 * | 5/2006 | Muller-Cohn | A01H 4/001 435/1.1 |
| 2006/0160164 A1 | 7/2006 | Miller et al. | |
| 2007/0099295 A1 * | 5/2007 | Maine | G01N 33/56905 435/345 |
| 2008/0038753 A1 * | 2/2008 | Branum et al. | 435/7.9 |
| 2009/0104634 A1 * | 4/2009 | Konrath et al. | 435/7.92 |
| 2010/0233175 A1 | 9/2010 | Yoshimura et al. | |
| 2011/0262992 A1 * | 10/2011 | Takagi | A61K 39/39591 435/188 |

FOREIGN PATENT DOCUMENTS

| | | | | | |
|---|---|---|---|---|---|
| CN | 101377505 | A | * | 3/2009 | |
| EP | 471293 | A2 | * | 2/1992 | ............. G01N 33/50 |
| EP | 0425633 | B1 | | 7/1994 | |
| EP | 273115 | B1 | | 9/1994 | |
| EP | 0424634 | B1 | | 6/1995 | |
| EP | 406473 | B1 | | 9/1995 | |
| EP | 326100 | B1 | | 9/1996 | |
| JP | 9249699 | A | | 9/1997 | |
| JP | 2002196000 | A | | 7/2002 | |
| JP | 2007192557 | A | | 8/2007 | |
| JP | 2008216237 | A | | 9/2008 | |
| JP | 2010127827 | A | | 6/2010 | |
| WO | WO 9964447 | A1 | * | 12/1999 | ............... C07K 7/04 |

(Continued)

OTHER PUBLICATIONS

Biocompare, retrieved from http://www.biocompare.com/24054-Zwitterionic-Detergents/2169150-Sulfobetaine-312-SB312-nDodecylNNdimethyl3ammonio1propanesulfonate/ on Jul. 30, 2013.*
Sentandreu et al., Monitoring of Chemical and Enzymatic Hydrolysis of Water-Soluble Proteins Using Flow-Injection Analysis with Fluorescence Detection and an Aqueous Eluant Containing 2-p-Toluidinylnaphthalene-6-Sulfonate as the Fluorescent Probe, Biotechnology and Bioengineering, 78(7), 829-833, 2002.*
International Search Report for International Application No. PCT/JP2012/063398 12 pages.*
Hemken et al., Performance Comparison of GP73, Fucosylated Hemopexin, PIVKA-II and AFP in a Cohort of Liver Disease Specimens, 1 pg, 2010, retrieved from http://www.promeddx.com/assets/84_abbott_2010_PIVKA-II_1-page.pdf on Oct. 27, 2016.*
Kinukawa et al., Epitope characterization of an anti-PIVKA-II antibody and evaluation of a fully automated chemiluminescent immunoassay for PIVKA-II, Clinical Biochemistry, vol. 48, Issues Nov. 16-17, 2015, pp. 1120-1125.*

(Continued)

*Primary Examiner* — Andrea S Grossman
(74) *Attorney, Agent, or Firm* — Melissa E. Kolom; Casimir Jones, S.C.

(57) ABSTRACT

Methods and kits for reducing non-specific binding in an immunoassay for PIVKA-II in a test sample are described, in which the test sample is reacted with an anti-prothrombin antibody in the presence of one or more of the following additives: skim milk, saponin, $CaCl_2$, $MgCl_2$, and a sulfobetaine zwitterionic detergent.

2 Claims, 7 Drawing Sheets

(56) References Cited

FOREIGN PATENT DOCUMENTS

| WO | 02/27613 A2 | 4/2002 |
|---|---|---|
| WO | WO2008124749 A1 | 10/2008 |

OTHER PUBLICATIONS

Abcam, Antibody Storage Guide, retrieved from http://www.abcam.com/protocols/antibody-storage-guide on Apr. 23, 2017, 3 pages.*
Machine translation of CN101377505.*
Kim et al., PIVKA-II Is a Useful Tumor Marker for Recurrent Hepatocellular Carcinoma after Surgical Resection, Oncology, 2007; 72:52-57 (abstract only).*
Akerstrom B., et al., "Protein G: A Powerful Tool for Binding and Detection of Monoclonal and Polyclonal Antibodies," Immunology, 1985, vol. 135 (4), pp. 2589-2592.
Asai D.J., "Antibodies in Cell Biology" in: Methods in Cell Biology, vol. 37, Academic Press Inc., 1993, Table of Contents.
Chevallet M., et al., "New Zwitterionic Detergents Improve the Analysis of Membrane Proteins by Two-Dimensional Electrophoresis," Electrophoresis, 1998, vol. 19 (11), pp. 1901-1909.
Clackson T., et al., "Making Antibody Fragments Using Phage Display Libraries," Nature, 1991, vol. 352, pp. 624-628.
Coligan J.E., et al., eds., "Peptides" in: Current Protocols in Immunology, Chapter 9, John Wiley and Sons, Inc., 1991, Table of Contents.
Griffiths A.D., et al., "Human Anti-Self Antibodies with High Specificity from Phage Display Libraries," European Molecular Biology Organization, 1993, vol. 12 (2), pp. 725-734.
Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the USA, 1988, vol. 85 (16), pp. 5879-5883.
Kohler G., et al., "Continuous Cultures of Fused Cells Secreting Antibody of Predefined Specificity," Nature, 1975, vol. 256 (5517), pp. 495-497.
Kronvall G., "A Surface Component in Group A, C, and G Streptococci with Non-Immune Reactivity for Immunoglobulin G," Journal of Immunology, 1973, vol. 111 (5), pp. 1401-1406.
Marks J.D., et al., "By-Passing Immunization: Building High Affinity Human Antibodies by Chain Shuffling," Biotechnology, 1992, vol. 10 (7), pp. 779-783.
Marks J.D., et al., "By-passing Immunization. Human Antibodies from V-gene Libraries Displayed on Phage," Journal of Molecular Biology, 1991, vol. 222 (3), pp. 581-597.
McCafferty J., et al., "Phage Antibodies: Filamentous Phage Displaying Antibody Variable Domains," Nature, 1990, vol. 348, pp. 552-554.
Paul W.E., Ed., Fundamental Immunology, Chapter 12, Raven Press, New York, 1989, pp. 332-336.
Stites D.P., et al., eds., "Basic and Clinical Immunology", 7th Edition, Appleton & Lange, 1991, Table of Contents.
Vaitukaitis J.L., "Production of Antisera with Small Doses of Immunogen: Multiple Intradermal Injections," Methods in Enzymology, 1981, vol. 73 (Pt B), pp. 46-52.
English Machine Translation of JP 2010127827 A.
English Machine Translation of JP 2008216237 A.
English Machine Translation of JP 2002196000 A.

* cited by examiner

IMMUNOASSAY METHODS AND REAGENTS FOR DECREASING NONSPECIFIC BINDING

RELATED APPLICATION INFORMATION

This application claims priority to U.S. Provisional Application Ser. No. 61/488,421 filed May 20, 2011, which is incorporated by reference in its entirety.

TECHNICAL FIELD

The present disclosure relates generally to immunoassay methods, reagents and kits for detecting a target analyte in a test sample, and in particular to immunoassay methods, reagents and kits for improving measurement of PIVKA-II in a sample by decreasing nonspecific antigen-antibody interactions.

BACKGROUND OF THE INVENTION

Immunoassay techniques have been known for the last few decades and are now commonly used in medicine for a wide variety of diagnostic purposes to detect target analytes in a test sample. Immunoassays exploit the highly specific binding of an antibody to its corresponding antigen, wherein the antigen is the target analyte. Typically, quantification of either the antibody or antigen is achieved through some form of labeling such as radio- or fluorescence-labeling. Sandwich immunoassays involve binding the target analyte in the sample to the antibody site (which is frequently bound to a solid support), binding labeled antibody to the captured analyte, and then measuring the amount of bound labeled antibody, wherein the label generates a signal proportional to the concentration of the target analyte inasmuch as labeled antibody does not bind unless the analyte is present in the sample.

Immunoassay methods can be carried out in any of a wide variety of formats. A typical heterogeneous sandwich immunoassay employs a solid phase as a support to which is bound a first (capture) antibody reactive with at least one epitope on the target analyte. A second (detection) antibody is also reactive with at least one epitope the target analyte, and may be conjugated to a detectable label that provides a signal that is measured after the detection antibody binds to the captured target analyte.

PIVKA-II ("Protein Induced by Vitamin K Absence or Antagonist-II"), also known as des-carboxy prothrombin (DCP), is a tumor marker useful for diagnosing and determining the prognosis of hepato-cellular carcinoma (HCC). PIVKA-II is also present in vitamin K deficiency or in patients using warfarin. Sensitivity of PIVKA-II detection methods can be important for establishing a diagnosis before clinical symptoms occur. Immunoassays for PIVKA-II are available, yet nonspecific binding interactions between the antibodies used and antigens other than PIVKA-II that may be present in a sample, reduce sensitivity and accuracy around the cutoff levels typically employed. Nonspecific antibody/antigen interactions can increase the risk of false positive diagnostic results and the risk that individuals will not obtain a diagnosis that is both timely and accurate. Methods for improving the sensitivity and accuracy of PIVKA-II immunoassays are therefore needed.

SUMMARY OF THE INVENTION

In one aspect, the present disclosure provides a method for measuring PIVKA-II in a test sample, the method comprising reacting the test sample with an anti-prothrombin antibody in the presence of at least one additive selected from the group consisting of: skim milk, saponin, $CaCl_2$, $MgCl_2$, and a sulfobetaine zwitterionic detergent. The additives may be provided in an immunoassay reagent comprising the antibody and effective amounts of the at least one additive. The antibody may comprise, for example, an anti-prothrombin monoclonal antibody, such as, for example, MCA1-8.

In another aspect, the present disclosure provides a method for improving sensitivity of a specific binding assay for PIVKA-II, wherein the specific binding assay comprises a first reaction producing a first complex comprising PIVKA-II bound to a first antibody capable of specifically binding PIVKA-II, and a second reaction including contacting the first complex with a second antibody capable of specifically binding PIVKA-II and conjugated to a detectable label, the method comprising: adding to the second reaction effective amounts of at least two compounds selected from the group consisting of skim milk, saponin, $CaCl_2$, $MgCl_2$, and a sulfobetaine zwitterionic detergent. In the above method, adding effective amounts of the at least two compounds to the second reaction may comprise, for example, adding a diluent to the second reaction, wherein the diluent comprises the second antibody and the effective amounts of the at least two compounds. The second antibody comprises, for example, an anti-prothrombin monoclonal antibody, such as, for example, MCA1-8.

In any of the methods, the immunoassay, also referred to as a specific binding assay, may be performed on a solid phase. The solid phase may comprise magnetic or paramagnetic microparticles. In any of the above methods, at least two, three or four additives can be used. In an exemplary method, two additives are used and these are skim milk and saponin. In any of the above methods, the sulfobetaine zwitterionic detergent may be selected from the group consisting of: n-Tetradecyl-N,N-dimethyl-3-ammonio-1-propanesulfonate (sold under ZWITTERGENT 3-14), n-Hexadecyl-N,N-dimethyl-3-ammonio-1-propanesulfonate (sold under ZWITTERGENT 3-16), n-Octadecyl-N,N-dimethyl-3-ammonio-1-propanesulfonate (sold under ZWITTERGENT 3-18), Amidosulfobetaine-14 (sold under ZWITTERGENT ASB-14), and Amidosulfobetaine-16 (sold under ZWITTERGENT ASB-16). For example, in an exemplary method, skim milk, saponin and n-Tetradecyl-N,N-dimethyl-3-ammonio-1-propanesulfonate (sold under ZWITTERGENT 3-14) are the selected additives. Alternatively, the selected additives may be skim milk, saponin and n-Hexadecyl-N,N-dimethyl-3-ammonio-1-propanesulfonate (sold under ZWITTERGENT 3-16). In another alternative, the selected additives are skim milk, saponin and n-Octadecyl-N,N-dimethyl-3-ammonio-1-propanesulfonate (sold under ZWITTERGENT 3-18). In still another alternative, the selected additives are a sulfobetaine zwitterionic detergent and one of $CaCl_2$ and $MgCl_2$, wherein the sulfobetaine zwitterionic detergent is selected from the group consisting of: n-Tetradecyl-N,N-dimethyl-3-ammonio-1-propanesulfonate (sold under ZWITTERGENT 3-14), n-Hexadecyl-N,N-dimethyl-3-ammonio-1-propanesulfonate (sold under ZWITTERGENT 3-16), and n-Octadecyl-N,N-dimethyl-3-ammonio-1-propanesulfonate (sold under ZWITTERGENT 3-18). In any of the methods, the immunoassay may comprise a competitive immunoassay. The immunoassay is may be carried out in an automated or semi-automated measuring apparatus. The immunoassay may comprise, for example, a sandwich assay.

In another aspect, the present disclosure provides an immunoassay reagent for improving sensitivity of a specific binding assay for PIVKA-II, the reagent comprising effective amounts of at least one additive selected from the group consisting of skim milk, saponin, $CaCl_2$ and $MgCl_2$ and a sulfobetaine zwitterionic detergent. The immunoassay reagent may include at least two, three or four of these additives.

In another aspect, the present disclosure provides a kit for performing an immunoassay for PIVKA-II, the kit comprising a specific binding reagent capable of specifically binding PIVKA-II, and at least one, or at least two, three or four additives selected from the group consisting of: skim milk, saponin, $CaCl_2$, $MgCl_2$, and a sulfobetaine zwitterionic detergent. In a kit, more than one additive may combined in an immunoassay reagent. The kit may further comprise instructions for reacting a test sample with antibody in the presence of the at least one, two, three or four additives, and for quantifying the amount of PIVKA-II in the test sample. The kit may further comprise a solid phase, which may comprise microparticles such as magnetic or paramagnetic microparticles.

DETAILED DESCRIPTION

Figure 1:
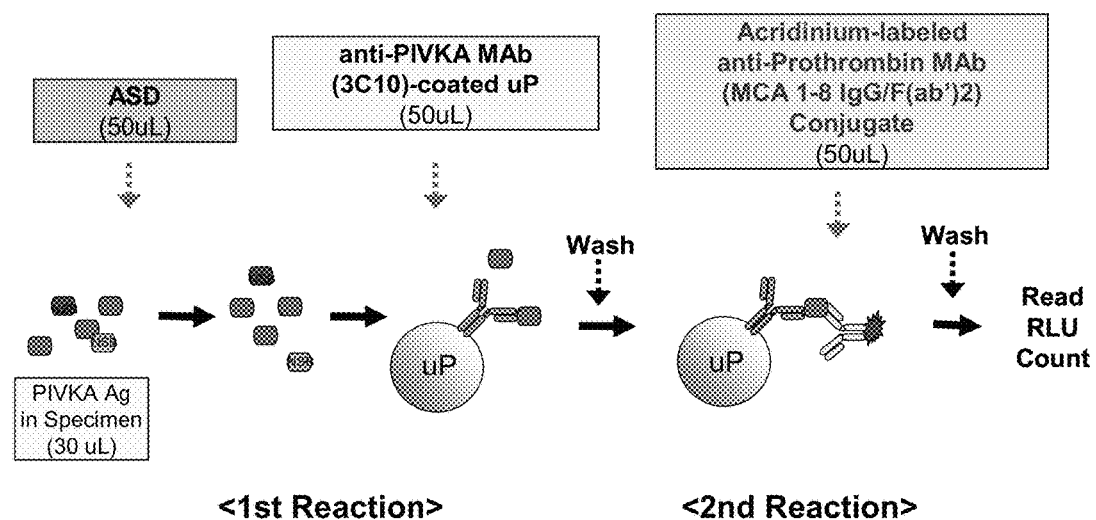
FIG. 1 is a schematic diagram of a sandwich immunoassay format for measuring PIVKA-II in a test sample, using a labeled anti-prothrombin monoclonal antibody (MCA 1-8 IgG/F(ab')2) conjugate.

The present disclosure provides improved assay methods, reagents and kits that improve specificity of immunoassays for detecting and measuring PIVKA-II in a test sample. The methods described herein are based in part on the finding that certain additives, when included alone or in combination in a conjugate diluent containing an anti-prothrombin MAb, can improve the sensitivity of an immunoassay for PIVKA-II. In particular, the additives skim milk, saponin, sulfobetaine zwitterionic detergents, $CaCl_2$ and $MgCl_2$, were found to improve the sensitivity of certain immunoassays for PIVKA-II when used alone or in any combination.

The assay methods as described herein can be applied to any assay system using a specific binding reagent capable of specifically binding PIVKA-II, including immunoassays performed using such binding reagents bound to a solid phase such as a magnetic or paramagnetic surface, and is also may be usefully carried out automated and semi-automated immunoassay systems.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" refers to approximately a +/−10% variation from the stated value. It is to be understood that such a variation is always included in any given value provided herein, whether or not it is specifically referred to.

Unless defined otherwise herein, all technical and scientific terms used herein have the same meaning as commonly understood by one of ordinary skill in the art to which this invention belongs.

a) Analyte

The term "analyte," as used herein, refers to the substance to be detected, which may be present in the sample (i.e., the biological sample). The analyte can be any substance having a naturally occurring specific binding partner or for which a specific binding partner can be prepared. Thus, an analyte is a substance that can bind to one or more specific binding partners in an immunoassay. One example of an analyte as described herein is an endogenous antigen, including but not limited to PIVKA-II, which is an antigen that can be assessed as a measure of, or measure of risk of developing, for example, hepatocellular carcinoma (HCC).

b) Binding Partner

The term "binding partner," as used herein, is a member of a binding pair, i.e., a pair of molecules wherein one of the molecules binds to the second molecule. Binding partners that bind specifically to one another are termed "specific binding partners." In addition to antigen and antibody binding partners commonly used in immunoassays, other specific binding partners include, for example, biotin and avidin, carbohydrates and lectins, complementary nucleotide sequences, effector and receptor molecules, cofactors and enzymes, enzyme inhibitors and enzymes, and the like. Furthermore, specific binding partners can include partner(s) that is/are analog(s) of the original specific binding partner, for example, an analyte-analog. Immunoreactive specific binding partners include antigens, antigen fragments, antibodies and antibody fragments, both monoclonal and polyclonal, and complexes thereof, including those formed by recombinant DNA methods.

c) Epitope

As used interchangeably herein, the terms "epitope", "epitopes" or "epitopes of interest" refer to a site(s) on any molecule that is recognized and is capable of binding to a complementary site(s) on its specific binding partner. The molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody, which may be an autoantibody. Typically an epitope is contained within a larger antigenic fragment (i.e., region or fragment capable of binding an antibody) and refers to the precise residues known to contact the specific binding partner. An antigenic fragment may contain more than one epitope.

d) Specific Binding

As used herein, the terms "specific binding", "specificity" and "specifically binding", characterize the interaction between two molecules having the ability to selectively react with one another as a pair (e.g., an antigen and antibody. The phrase "specifically binds to" refers for example to the ability of an antibody to specifically bind to its target antigen (e.g., an endogenous antigen such as PIVKA-II), while not specifically bind to other entities. Antibodies or antibody fragments that specifically bind to an analyte can be identified, for example, by diagnostic immunoassays (e.g., radioimmunoassays ("RIA") and enzyme-linked immunosorbent assays ("ELISAs") (See, for example, Paul, ed., Fundamental Immunology, 2nd ed., Raven Press, New York, pages 332-336 (1989)), surface plasmon resonance (e.g., sold under BIACORE, Sweden), kinetic exclusion assay (e.g., sold under KINEXA, available from Sapidyne Instruments (Boise, Id.)) or other techniques known to those of skill in the art. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

e) Solid Phase

A "solid phase," as used herein, refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

f) Microparticle

As used herein, term "microparticle" refers to a small particle that is recoverable by ultracentrifugation. Microparticles typically have an average diameter on the order of about 1 micron or less.

g) Detectable Label

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like. As used with reference to a labeled detection agent, a "direct label" is a detectable label that is attached, by any means, to the detection agent. As used with reference to a labeled detection agent, an "indirect label" is a detectable label that specifically binds the detection agent. Thus, an indirect label includes a moiety that is the specific binding partner of a moiety of the detection agent. Biotin and avidin are examples of such moieties that are employed, for example, by contacting a biotinylated antibody with labeled avidin to produce an indirectly labeled antibody. Preferred detectable labels include acridinium compounds such as those described, for example, in U.S. Pat. Nos. 5,543,524; 5,565,570; 5,783,699; EP-A 830629, and acridinium-9-carboxylate phenyl esters as described in WO 2008/124749. An indicator reagent may be used to contact a detectable label to produce a detectable signal. Thus, for example, in conventional enzyme labeling, an antibody labeled with an enzyme can be contacted with a substrate (the indicator reagent) to produce a detectable signal, such as a colored reaction product.

h) Antibody

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CHI by a disulfide bond. The F(ab')2 may be reduced under mild conditions to break the disulfide linkage in the hinge region thereby converting the $(Fab')_2$ dimer into a Fab' monomer. The Fab' monomer is essentially a Fab with part of the hinge region (see, FUNDAMENTAL IMMUNOLOGY, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) PROC. NAT. ACAD. SCI. USA, 85: 5879-5883. While the VH and VL are connected to each as a single polypeptide chain, the VH and VL domains associate non-covalently. The scFv antibodies and a number of other structures converting the naturally aggregated, but chemically separated, light and heavy polypeptide chains from an antibody V region into a molecule that folds into a three dimensional structure substantially similar to the structure of an antigen-binding site are known to those of skill in the art (see, e.g., U.S. Pat. Nos. 5,091,513, 5,132,405, and 4,956,778).

i) Test Sample

As used herein, the term "test sample" generally refers to a biological material being tested for and/or suspected of containing a target analyte, i.e., an analyte of interest, e.g., PIVKA-II. The biological material may be derived from any biological source but preferably is a biological fluid likely to contain the target analyte. Examples of biological materials include, but are not limited to, stool, whole blood, serum, plasma, red blood cells, platelets, bronchial lavage, bone marrow aspirate, pleural effusion, interstitial fluid, saliva, ocular lens fluid, cerebrospinal fluid, sweat, urine, ascites fluid, mucous, nasal fluid, sputum, synovial fluid, peritoneal fluid, vaginal fluid, menses, amniotic fluid, semen, as well as tumor tissue or any other bodily constituent or any tissue culture supernatant that could contain the analyte of interest. An exemplary test sample for the methods described herein is derived from whole blood, serum or plasma. Test samples may be obtained by routine procedures such as but not limited to venipuncture, tissue biopsy including needle biopsy, swab, wipe, and fluid collection. Test samples are obtained from an animal, preferably a mammal, and more preferably a human.

The test sample may be used directly as obtained from the biological source or following a pretreatment to modify the character of the sample. For example, such pretreatment may include preparing plasma from blood, diluting viscous fluids and so forth. Methods of pretreatment may also involve centrifugation, filtration, precipitation, dilution, distillation, mixing, concentration, inactivation of interfering components, the addition of reagents, lysing, etc. If such methods of pretreatment are employed with respect to the test sample, such pretreatment methods are such that the target analyte remains in the test sample at a concentration proportional to that in an untreated test sample (e.g., namely, a test sample that is not subjected to any such pretreatment method(s)).

B. Immunoassays for Pivka-II i. Immunoassays

PIVKA-II is often measured as part of a clinical diagnosis of hepatic cell cancer (also referred to as hepatocellular carcinoma, or HCC) in patients. Typically PIVKA-II is measured from a serum or plasma sample and subjected to an immunoassay, which can be performed, for example on a solid phase such as magnetic beads, glass beads, plastic plates, latexes and the like on which a PIVKA-II specific monoclonal or polyclonal antibody is adsorbed. The coated solid phase is then contacted with the serum or plasma, resulting in a first reaction forming a complex of any PIVKA-II antigen in the sample with the anti-PIVKA-II antibody. Following a wash of the reaction mixture for separation of bound versus free (B/F) antigen, a second reaction is carried out by adding human prothrombin specific polyclonal or monoclonal antibody labeled with a detectable label, such as but not limited to an enzyme, fluorescent material, or radioisotope. Following a second wash for B/F separation, measurement is taken of the absorbance or luminescence of the detectable label, as bound to the immune complex formed by the antigen-antibody reaction, to determine the amount of PIVKA-II in the serum or the plasma.

Non-specific interactions, particularly of the prothrombin specific antibody with antigens other than PIVKA-II that may be present in the sample, may interfere and reduce the sensitivity of the assay as described above. Non-specific interactions may arise because of impurities of the antibodies, the similarity of thrombin to the target antigen (PIVKA-II), or because of physical adsorbtion of other antigens onto the solid phase (the magnetic beads, glass beads, and the like), which can give rise to false positive detection and thus inaccurate measurements.

As described herein, sensitivity and specificity of an immunoassay for PIVKA-II can be improved by including in the immunoassay reagents certain additives. The present disclosure thus provides methods for improving sensitivity of an immunoassay for PIVKA-II. In the methods, the additives include at least one selected from skim milk, saponin, $CaCl_2$, $MgCl_2$, and a sulfobetaine zwitterionic detergent. The one or more additives are added to an immunoassay reaction in which a test sample that may contain PIVKA-II is contacted with an anti-prothrombin antibody that is capable of specifically binding PIVKA-II. To obtain the best improvement of sensitivity, at least two or at least three of the additives are used in the assay. The additive(s) may be added separately to the reaction, or may be provided in a single composition such as an assay diluent, particularly for example in a conjugate diluent containing a labeled anti-prothrombin antibody, for example a monoclonal antibody used as a detection reagent in a sandwich assay format. Thus, in the PIVKA-II immunoassay methods as described herein, it is possible to reduce or eliminate the influence of inhibiting substances that may be present in the test sample, without resort to substantial dilution of the sample, or using a large amount of an assay buffer solution. At the same time, the improved PIVKA-II immunoassay simply and conveniently provides a highly sensitive and reliable measurement of PIVKA-II in the sample. This is particularly advantageous where the immunoassay is carried out on a fully automated or semi-automated system and a large amount of sample is to be tested within a short time.

While the methods described herein relate to a PIVKA-II immunoassay, reagents and kits, it is expected that the methods may be more generally applied to immunoassays for other target analytes, and that inclusion of at least one of the additives as described herein when reacting a test sample with an antibody against an antigen of interest, can improve sensitivity of measurements of other target analytes in test samples.

Methods of the present disclosure may also be applied to any of a variety of immunoassay formats. These formats are simply modified to include one or more additives as described herein, in a specific binding reaction in which the analyte antigen (e.g., PIVKA-II) reacts with an anti-prothrombin antibody. For a general review of immunoassays, see METHODS IN CELL BIOLOGY VOLUME 37: ANTIBODIES IN CELL BIOLOGY, Asai, ed. Academic Press, Inc. New York (1993); and BASIC AND CLINICAL IMMUNOLOGY 7TH EDITION, Stites & Terr, eds. (1991), the disclosures of which are incorporated by reference in their entireties. The methods as described herein can be applied to any immunoassay format provided that it utilizes a specific antigen-antibody reaction, the sensitivity of which might be negatively affected by non-specific interactions. Accordingly, it can be applied to any routinely employed immunoassay formats, including but not limited to a competitive immunoassay format and a non-competitive immunoassay format such as a sandwich format. In a non-competitive immunoassay, the amount of analyte can be measured according to a known, positive correlation of the amount of analyte bound to antibody with the concentration of analyte present in the test sample Immunoassays may employ a capture agent, which is a binding partner that binds to the target analyte/antigen, for example to PIVKA-II. Capture agents useful in the immunoassay methods of the present disclosure include those that bind to the target analyte (e.g., PIVKA-II), including antibodies specific for the target analyte. Capture agents can be attached to a solid phase. When a solid phase is used, binding of a solid phase-affixed capture agent to the target analyte forms a solid phase-affixed complex. A labeled detection agent may also be used, which is a specific binding partner such as an antibody capable of specifically binding the target analyte, such as PIVKA-II, that is directly or indirectly labeled with a detectable label such as but not limited to an enzyme, fluorescent material, or radioisotope. The specific binding partner in the detection agent may be, for example, an anti-prothrombin antibody, which can be for example an anti-prothrombin monoclonal antibody. Upon reaction of the detection reagent with the solid-phase-affixed complex, a "sandwich" is formed in which the target analyte is bound between the two antibody reagents. The bound entities are separated, if necessary, from free labeled antibody, typically by washing, and the signal from the bound label is detected/quantitated by detecting complex(es) comprising the antigen bound to the reactive antibodies. In an exemplary format of a sandwich immunoassay, detecting the analyte comprises detecting a signal from the solid phase-affixed complex.

FIG. 1 shows an exemplary immunoassay format for measuring PIVKA-II, in which PIVKA-II is measured via a two-step, chemiluminescence sandwich format. For example, a test sample ("specimen") containing the target analyte, e.g., PIVKA-II, contacts the first antibody, and the first antibody captures the target analyte. As shown in FIG. 1, the first antibody can be, for example, an anti-PIVKA-II monoclonal antibody such as 3C10 as described in U.S. patent application Ser. No. 12/401,361 (published as US 2010/0233175). The first antibody is optionally coated onto a solid phase such as microparticles, as shown in FIG. 1. Following a wash to remove free, unbound antigen, a first complex is formed by target analyte (i.e., antigen, for example PIVKA-II) bound to the first antibody. The first complex is then contacted with a second, labeled antibody capable of specifically binding PIVKA-II. As shown in FIG. 1, the second reaction may be carried out by adding a human prothrombin specific antibody, preferably a monoclonal antibody labeled with a detectable label as described elsewhere herein. As shown in FIG. 1, for example, the anti-prothrombin antibody can be the anti-prothrombin monoclonal antibody MCA 1-8 IgG (available from Atto Mol Inc., 5F Nishiikesankei Bldg. 3-23-7 Nishiikebukuro, Toshimaku, Tokyo, Japan), or MCA 1-8 F(ab')2, and the label may be an acridinium compound. After allowing sufficient time for binding of the second, labeled antibody to the first complex to occur, the resulting second complex consists of the first antibody, antigen (target analyte PIVKA-II) and second antibody, optionally bound to the solid phase. Following a second wash to remove unbound antigen, measurement is taken of the signal, e.g., absorbance or luminescence generated by the detectable label, wherein the signal generated by the second, labeled antibody is proportional to the concentration of the target analyte as determined by the rate of formation (k1) of the immunodetection complex versus the rate of dissociation of the immunodetection complex (k2).

An analyte including PIVKA-II for example, can also be measured in competitive immunoassay, wherein the signal is negatively correlated with the concentration of analyte present in the test sample. In an exemplary competitive format, the test sample is contacted with an antibody, which may or may not be affixed to a solid phase, and also is contacted with a competing, labeled antigen. The labeled antigen may be indirectly or directly labeled. This step is carried out under conditions sufficient for specific binding of the labeled antigen and analyte antigen to the antibody. The labeled antigen and analyte antigen compete with each other for binding to the antibody. Accordingly, the higher the level of analyte antigen (such as PIVKA-II) in a test sample, the lower is the binding of labeled antigen to the antibody. The test sample may be contacted with the labeled antigen and the antibody either simultaneously or sequentially, in any order. Competitive immunoassays of this type can also be conveniently carried out using a solid phase-affixed antibody. In this case, binding of the analyte antigen present in the test sample to antibody forms a solid phase-affixed complex, and detection entails detecting a signal from the solid phase-affixed complex. The bound entities are separated, if necessary, from free labeled antigen, typically by washing, and the signal from any bound label (displacing analyte antigen) is detected.

To improve sensitivity of a PIVKA-II immunoassay as described herein, a PIVKA-II immunoassay may be modified by contacting a test sample suspected of containing PIVKA-II, with an antibody capable of specifically binding PIVKA-II, in the presence of one or more additives as described herein, under conditions sufficient for binding of the antibody to any PIVKA-II present in the test sample. PIVKA-II is detected/quantified by detecting complex(es) comprising PIVKA-II antigen bound to the reactive antibody.

Addition of the selected additives as described below to an immunoassay diluent can reduce background, non-specific binding and enhance antigen-antibody interaction. As described herein, the additives can be used to improve sensitivity of a PIVKA-II assay. Additives that can be used alone or in combination in the immunoassays as described herein include: skim milk, saponin, $CaCl_2$, $MgCl_2$, and a sulfobetaine zwitterionic detergent. Any sulfobetaine-type detergent may be used, including but not limited to n-Tetradecyl-N,N-dimethyl-3-ammonio-1-propanesulfonate (sold under ZWITTERGENT 3-14), n-Hexadecyl-N,N-dimethyl-3-ammonio-1-propanesulfonate (sold under ZWITTERGENT 3-16), n-Octadecyl-N,N-dimethyl-3-ammonio-1-propanesulfonate (sold under ZWITTERGENT 3-18), Amidosulfobetaine-14 (sold under ZWITTERGENT ASB-14), and Amidosulfobetaine-16 (sold under ZWITTERGENT ASB-16), preferably n-Tetradecyl-N,N-dimethyl-3-ammonio-1-propanesulfonate (sold under ZWITTERGENT 3-14), n-Hexadecyl-N,N-dimethyl-3-ammonio-1-propanesulfonate (sold under ZWITTERGENT 3-16), and n-Octadecyl-N,N-dimethyl-3-ammonio-1-propanesulfonate (sold under ZWITTERGENT 3-18). In an exemplary method, n-Hexadecyl-N,N-dimethyl-3-ammonio-1-propanesulfonate (sold under ZWITTERGENT 3-16) is used. For convenience of reference and in keeping with common practice in the literature, product names are used herein to refer to these sulfobetaine detergents, the corresponding chemical names of which are as follows:

3-(N,N-Dimethyloctylammonia)propane-sulfonate sold under ZWITTERGENT 3-8 n-Decyl-N,N-dimethyl-3-ammonio-1-propanesulfonate sold under ZWITTERGENT 3-10

N-Dodecyl-N,N-dimethyl-3-amino-1-propanesulfonate sold under ZWITTERGENT 3-12 n-Tetradecyl-N,N-dimethyl-3-ammonio-1-propanesulfonate sold under ZWITTERGENT 3-14 n-Hexadecyl-N,N-dimethyl-3-ammonio-1-propanesulfonate sold under ZWITTERGENT 3-16 n-Octadecyl-N,N-dimethyl-3-ammonio-1-propanesulfonate sold under ZWITTERGENT 3-18 (also sold as ANZERGENT 3-18 by Affymetrix Inc., Santa Clara, Calif.)

"Amidosulfobetaine-14"; 3-[N,N-Dimethyl(3-myristoylaminopropyl)ammonio]propanesulfonate sold under ZWITTERGENT ASB-14

"Amidosulfobetaine-16" sold under ZWITTERGENT ASB-16.

Sulfobetaine-type zwitterionic detergents are available from multiple commercial sources, including the CALBIOCHEM brand synthetic zwitterionic brand detergents sold under the name ZWITTERGENT by the EMD Biosciences Group of Merck Chemicals. Sulfobetaine-type zwitterionic detergents are also available from multiple other commercial sources, including for example Sigma-Aldrich Co. (St. Louis, Mo.), and from Affymetrix, Inc. (Santa Clara, Calif.) under the name ANZERGENT). The ASB detergents are also described, for example, in M. Chevallet et al, ELECTROPHORESIS 19: 1901 (1998).

"Skim milk" refers to any cow milk from which cream has been removed such that the milk contains less than 1% butterfat. Saponin can be any commercially available plant-derived saponin prepared by a controlled manufacturing process, for example such as those made from the soap bark tree (*Quillaja saponaria*), and other sources and available for example from Sigma-Aldrich Co. (St. Louis, Mo.), and Mallinckrodt Baker (Phillipsburg, N.J.). Saponin is typically provided as a crystalline powder. Amounts for each additive, when included as an additive, are provided in Table 1 below, wherein the amounts for any solid (e.g., powdered) additive given as % w/v, and the amounts for liquid additives encompass % w/v or % v/v:

TABLE 1

| Diluent Additives | | |
|---|---|---|
| Additive | Amount Range | Exemplary Amounts |
| Skim milk | 1.00%-5.00% | 1.00%, 1.25%, 1.67%, 3.00% |
| Saponin | 1.00%-5.00% | 1.00% |
| $CaCl_2$ | 30 mM-200 mM | 30 mM, 50 mM, 100 mM, 150 mM |
| $MgCl_2$ | 30 mM-200 mM | 30 mM, 50 mM, 100 mM, 150 mM |
| sulfobetaine zwitterionic detergent | 1.00%-5.00% | 1.00%, 1.2%, 1.6%, 3.00% | ii. Antibodies

Antibodies useful in the immunoassay methods described herein include polyclonal and monoclonal antibodies. Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

The methods can be applied to immunoassays that utilize reagents comprising a polyclonal or monoclonal antibody, a chimeric antibody, a human antibody, an affinity maturated antibody or fragments of said antibodies (such as an Fab, Fab', or Fab'2 fragment) or combinations of polyclonal, monoclonal and antibody fragments where only the active site is taken out by means of genetic recombination, so long the antibody provides specific reactivity with the analyte of interest, for example PIVKA-II. As those of skill in the art readily appreciate, antibodies can be prepared by any of a number of commercial services (e.g., Berkeley Antibody Laboratories, Bethyl Laboratories, Anawa, Eurogenetec, etc.). Antibodies used are preferably those that are able to recognize PIVKA-II, which may include an anti-prothrombin antibody.

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique involves isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas are screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

While monoclonal antibodies are highly specific to the analyte/antigen, a polyclonal antibody can preferably be used as each capture antibody to immobilize as much of the analyte/antigen as possible. A monoclonal antibody with inherently higher binding specificity for the analyte/antigen may then preferably be used for each detection antibody. In any case, when capture and detection antibodies are used, each recognizes non-overlapping epitopes on the target analyte, and preferably is capable of binding simultaneously to different epitopes on the target analyte, each without interfering with the binding of the other.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen. If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal. The antibodies are then obtained from blood samples taken from the animal. The techniques used to produce polyclonal antibodies are extensively described in the literature (see, e.g., Methods of Enzymology, "Production of Antisera with Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies (see, e.g., Coligan, et al. (1991) Unit 9, CURRENT PROTOCOLS IN IMMUNOLOGY, Wiley Interscience).

If desired, the endogenous antigen (i.e., analyte of interest) may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., METHODS OF ENZYMOLOGY, "Production of Antisera with Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound (see, e.g., Coligan, et al. (1991)).

As used herein, the term "antibody" encompasses antigen-binding antibody fragments, e.g., single chain antibodies (scFv or others), which can be produced/selected using phage display or yeast display technology. The ability to express antibody fragments on the surface of viruses that infect bacteria (bacteriophage or phage) makes it possible to isolate a single binding antibody fragment, e.g., from a library of greater than 1010 nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) NATURE 348: 552-554; Hoogenboom et al. (1991) NUCLEIC ACIDS RES. 19: 4133-4137).

Since the antibody fragments on the surface of the phage are functional, phage-bearing antigen-binding antibody fragments can be separated from non-binding phage by antigen affinity chromatography (McCafferty et al. (1990) NATURE 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) NATURE 348: 552-554). Thus, even when enrichments are low (Marks et al. (1991) J. MOL. BIOL. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. MOL. BIOL. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naive" phage antibody library, binding antibody fragments have been isolated against more than 17 different antigens, including haptens, polysaccharides, and proteins (Marks et al. (1991) J. MOL. BIOL. 222: 581-597; Marks et al. (1993). BIO/TECHNOLOGY 10: 779-783; Griffiths et al. (1993) EMBO J. 12: 725-734; Clackson et al. (1991) NATURE 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. MOL. BIOL. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can also be prepared by any of a number of commercial services (e.g., Berkeley Antibody Laboratories, Bethyl Laboratories, Anawa, Eurogenetec, etc.).

iii. Solid Phase

Immunoassays according to the present disclosure may employ a solid phase as a support for the capture agent. The solid phase can be any suitable material with sufficient surface affinity to bind a capture agent. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like.

Nitrocellulose has excellent absorption and adsorption qualities for a wide variety of reagents including monoclonal antibodies. Nylon also possesses similar characteristics and also is suitable.

Preferred solid phase materials for flow-through assay devices include filter paper such as a porous fiberglass material or other fiber matrix materials. The thickness of such Material is not critical and will be a matter of choice, largely based upon the properties of the test sample or analyte being assayed, such as the fluidity of the test sample.

Alternatively, the solid phase can constitute microparticles. Microparticles useful in the present disclosure can be selected by one skilled in the art from any suitable type of particulate material and include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field.

Microparticles can be suspended in the mixture of soluble reagents and test sample or can be retained and immobilized by a support material. In the latter case, the microparticles on or in the support material are not capable of substantial movement to positions elsewhere within the support material. Alternatively, the microparticles can be separated from suspension in the mixture of soluble reagents and test sample by sedimentation or centrifugation. When the microparticles are magnetic or paramagnetic the microparticles can be separated from suspension in the mixture of soluble reagents and test sample by a magnetic field.

The methods of the present invention can be adapted for use in systems that utilize microparticle technology including automated and semi-automated systems wherein the solid phase comprises a microparticle. Such systems include those described in pending U.S. application Ser. No. 425, 651 and U.S. Pat. No. 5,089,424, which correspond to published EPO App. Nos. EP 0 425 633 and EP 0 424 634, respectively, and U.S. Pat. No. 5,006,309.

The solid phase may include one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714. The basic method is described further below with respect to electrochemical detection.

The capture agent can be attached to the solid phase by adsorption, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase. Ion capture procedures for immobilizing an immobilizable reaction complex with a negatively charged polymer, described in U.S. application Ser. No. 150,278, corresponding to EP Publication No. 0326100, and U.S. application Ser. No. 375,029 (EP Publication No. 0406473), can be employed according to the present invention to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in U.S. application Ser. No. 921,979, corresponding to EPO Publication No. 0 273,115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercaptopropyl)-trimethoxy silane (Sigma Chemical Co., St. Louis, Mo.) can be used to introduce reactive groups such as amino-, vinyl, and thiol, respectively. Such activated surfaces can be used to link the capture agent directly (in the cases of amino or thiol), or the activated surface can be further reacted with linkers such as glutaraldehyde, bis(succinimidyl)suberate, SPPD 9 succinimidyl 3-[2-pyridyldithio]propionate), SMCC (succinimidyl-4-[Nmaleimidomethyl]cyclohexane-1-carboxylate), SIAB (succinimidyl[4iodoacetyl]aminobenzoate), and SMPB (succinimidyl 4-[1maleimidophenyl]butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. application Ser. No. 150,278, filed Jan. 29, 1988, and U.S. application Ser. No. 375,029, filed Jul. 7, 1989, each of which is incorporated herein by reference.

Other considerations affecting the choice of solid phase include the ability to minimize nonspecific binding of labeled entities and compatibility with the labeling system employed. For, example, solid phases used with fluorescent labels should have sufficiently low background fluorescence to allow signal detection. Following attachment of a specific capture agent, the surface of the solid support may be further treated with materials such as serum, proteins, or other blocking agents to minimize nonspecific binding.

iv. Detectable Labels

As discussed above, many immunoassays according to the present disclosure employ a labeled detection agent, such as a labeled antibody or a labeled antigen.

Detectable labels suitable for use in the detection agents of the present invention include any composition detectable by spectroscopic, photochemical, biochemical, immunochemical, electrical, optical, or chemical means. Useful labels in the present invention include magnetic beads (e.g., sold under DYNABEADS), fluorescent dyes (e.g., fluorescein, Texas Red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminal and the like, radiolabels (e.g., 3H, 125I, 35S, 14C, or 32P), catalysts such as enzymes (e.g., horseradish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the test sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected. In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, e.g., Kronval, et al. (1973) J. IMMUNOL., 111: 1401-1406, and Akerstrom (1985) J. IMMUNOL., 135: 2589-2542). Such polypeptides can thus be labeled and added to the assay mixture, where they will bind to the detection antibody, as well as to the species-specific antibody, labeling both and providing a composite signal attributable to analyte and autoantibody present in the test sample.

Some labels useful in the present disclosure may require the use of an indicator reagent to produce a detectable signal. In an ELISA, for example, an enzyme label (e.g., beta-galactosidase) will require the addition of a substrate (e.g., X-gal) to produce a detectable signal.

The present invention is for example applicable (e.g., adaptable) to the jointly owned commercial Abbott Point of Care electrochemical immunoassays system (sold under I-STAT) which performs sandwich immunoassays for several different antigens. Immunosensors and ways of operating them in single-use test devices are described in jointly owned Publication Nos. US 20030170881, US 20040018577, US 20050054078, and US 20060160164, each of which is incorporated herein by reference. Additional background on the manufacture of electrochemical and other types of immunosensors is found in jointly owned U.S. Pat. No. 5,063,081 which is also incorporated by reference.

The present disclosure may also be applied to multiple immunoassay formats, for simultaneously assaying multiple analytes in one test sample. For example, the solid phase can include a plurality of different capture agents, including one that captures endogenous antigen or analyte of interest (e.g., PIVKA-II). Thus, for example, the solid phase can have affixed thereon a plurality of antibodies, wherein each is intended to test for the presence of different analytes (e.g., PIVKA-II and other endogenous analytes) in the test sample. In an exemplary embodiment, the solid phase can consist of a plurality of different regions on a surface, wherein each region has a particular antibody affixed therein.

Multiplex formats can, but need not, employ a plurality of labels, wherein each label is used for the detection of a particular antigen. For example, multiple, different analytes can be detected without using a plurality of labels where a plurality of capture agents, such as antibodies having different specificities, are affixed to the solid phase at different known locations. Because the specificity of the capture agent at each location is known, the detection of a signal at a particular location can be associated with the presence of antigen bound at that location. Examples of this format include microfluidic devices and capillary arrays, containing different capture agents at different locations along a channel or capillary, respectively, and microarrays, which typically contain different capture agents arranged in a matrix of spots ("target elements") on a surface of a solid support. Each different capture agent can be affixed to a different electrode, which can, for example, be formed on a surface of a solid support, in a channel of a microfluidic device, or in a capillary.

Optionally the immunoassays as described herein can be used in kits for commercial platform immunoassays including, for example, chemiluminescent microparticle immunoassays (CMIA) for the qualitative detection of target antigen, e.g., PIVKA-II blood screening assays on Abbott's EIA (Bead) platform, and/or the platforms sold by Abbott under PRISM, AXSYM, AND/OR ARCHITECT c-system or i-system, as well as in other commercial and/or in vitro diagnostic assays.

C. Test Kits

The present disclosure also provides test kits for assaying test samples for analytes such as PIVKA-II and other endogenous antigens. Test kits according to the present disclosure include one or more reagents useful for practicing one or more immunoassays according to the present disclosure. A kit generally includes a package with one or more containers holding the reagents, as one or more separate compositions or, optionally, as admixture where the compatibility of the reagents will allow. The kit can also include other material(s), which may be desirable from a user standpoint, such as a buffer(s), a diluent(s), a standard(s), and/or any other material useful in sample processing, washing, or conducting any other step of the assay.

For example, according to the present disclosure, a kit for performing a specific binding assay of PIVKA-II in a test sample, may include a container holding a modified assay diluent containing any one or more of the diluent additives as described herein above, i.e., skim milk, saponin, $CaCl_2$, $MgCl_2$, and a sulfobetaine zwitterionic detergent, including not limited to n-Tetradecyl-N,N-dimethyl-3-ammonio-1-propanesulfonate (sold under ZWITTERGENT 3-14), n-Hexadecyl-N,N-dimethyl-3-ammonio-1-propanesulfonate (sold under ZWITTERGENT 3-16), n-Octadecyl-N,N-dimethyl-3-ammonio-1-propanesulfonate (sold under ZWITTERGENT 3-18), Amidosulfobetaine-14 (sold under ZWITTERGENT ASB-14), and Amidosulfobetaine-16 (sold under ZWITTERGENT ASB-16), preferably n-Tetradecyl-N,N-dimethyl-3-ammonio-1-propanesulfonate (sold under ZWITTERGENT 3-14), n-Hexadecyl-N,N-dimethyl-3-ammonio-1-propanesulfonate (sold under ZWITTERGENT 3-16), and n-Octadecyl-N,N-dimethyl-3-ammonio-1-propanesulfonate (sold under ZWITTERGENT 3-18). Alternatively, a kit may one or more additives in individual containers and each additive can be combined with assay diluent preparation to prepare a modified assay diluent as described herein, in preparation for performing the immunoassay. If desired, any of the additives can be included in the test kit in multiple concentrations. The additives can be included in the kit in any amount convenient for preparing an assay diluent that contains each additive in an amount as described herein above.

Kits according to the present disclosure can include one or more first or capture antibodies, each of which binds to at least one epitope on the target analyte (e.g., PIVKA-II), and one or more second or detection antibodies, each of which binds to at least one epitope on the target analyte (e.g., PIVKA-II) that is different from any epitope to which any of the capture antibodies bind, and further instructions for detecting or quantifying the target analyte.

Kits according to the present disclosure can include a solid phase and a capture agent affixed to the solid phase, wherein the capture agent is an antibody specific for the analyte being assessed in the test sample. The solid phase may comprise a material such as a magnetic or paramagnetic particle including a microparticle, a bead, a test tube, a microtiter plate, a cuvette, a membrane, a scaffolding molecule, a quartz crystal, a film, a filter paper, a disc or a chip. An exemplary kit contains magnetic or paramagnetic microparticles coated with the first (capture) antibody capable of specifically binding PIVKA-II, or electrodes. Test kits designed for multiplex assays conveniently contain one or more solid phases including a plurality of antibodies that are specific for a plurality of different analytes of interest (e.g., PIVKA-II and other endogenous antigens). Thus, for example, a test kit designed for multiplex electrochemical immunoassays can contain a solid phase including a plurality of electrodes, with each electrode bearing a different antibody.

Where such kits are to be employed for conducting sandwich immunoassays, the kits can additionally include a labeled antibody as a detection reagent. For example, a kit may include at least one direct label, which may be an enzyme, oligonucleotide, nanoparticle chemiluminophore, fluorophore, fluorescence quencher, chemiluminescence quencher, or biotin. In an exemplary embodiment, the direct label is an acridinium compound, such as acridinium-9-carboxamide. For example, a kit may further include an acridinium-labeled conjugate comprising an acridinium compound attached to a second, detection antibody capable of specifically binding the target analyte. Test kits according to the present disclosure can instead or in addition also include at least one indirect label. If the label employed generally requires an indicator reagent to produce a detectable signal, the test kit preferably includes one or more suitable indicator reagents.

A kit may contain polyclonal or non-human monoclonal antibodies against the target analyte, including for example mouse monoclonal antibodies, and these may be used as capture and/or detection antibodies. For example, a kit for measuring the amount of PIVKA-II in a serum- or plasma-containing test sample may include a first antibody comprising a mouse, monoclonal anti-PIVKA-II antibody such as, for example, 3C10 (see U.S. patent application Ser. No. 12/401,361, published as US 2010/0233175), and a second antibody comprising a mouse, monoclonal anti-prothrombin antibody such as, for example, MCA 1-8 IgG (Atto Mol Inc., 5F Nishiikesankei Bldg. 3-23-7 Nishiikebukuro, Toshimaku, Tokyo, Japan), or MCA 1-8 F(ab')2.

An exemplary kit may thus contain components including but not limited to a first, anti-PIVKA-II antibody, which may be a mouse, monoclonal antibody, which is coated on magnetic or paramagnetic microparticles in a buffer, preferably TRIS buffer, and even more preferably with protein (bovine) stabilizers and antimicrobial agents as a preservative. The kit may further contain an acridinium-labeled conjugate comprising a mouse anti-prothrombin monoclonal antibody in buffer, preferably in MES (2-[N-Morpholino]ethanesulfonic acid) buffer, with protein (bovine) stabilizers and antimicrobial agents as a preservative; and a modified assay diluent comprising a buffer, preferably TRIS, containing one or more diluent additives as described herein. Preferably the assay diluent also includes antimicrobial agents as preservatives. For immunoassays using acridinium-labeled conjugate, a kit may also comprise a Pre-Trigger Solution containing 1.32% (wt/vol) hydrogen peroxide; a Trigger Solution containing 0.35 N sodium hydroxide; and a wash buffer containing phosphate buffered saline solution and an antimicrobial agent preservative.

D. Adaptations of the Methods of the Present Disclosure

By way of example, not of limitation, examples of the present invention shall now be given.

Example 1: Comparative Study of Candidate Additives for MCA1-8 Conjugate Diluent The automated PIVKA-II immunoassay protocol (sold by Abbott Laboratories, Abbott Park, Ill., 60035-6050 under ARCHITECT) is performed as follows: previously prepared anti-PIVKA-II antibody such as anti-PIVKA MAb 3C10 is purified and coated to magnetic microparticles (Abbott Laboratories, IL), to the surface of which is attached a carboxyl group via a covalent bond using 1-Ethyl-3-[3-dimethylaminopropyl]carbodiimide hydrochloride (EDC). The coated microparticles are dispersed into buffer solution including bovine serum albumin (BSA) and to prepare Reagent A. Anti-Prothrombin antibody (code # PA150) from Hyphen Biomed (France), labeled by N-hydroxysuccinimide (NHS) activated acridinium ester (Abbott Laboratories, IL) is diluted into the buffer containing BSA to prepare Reagent B. Buffer solution including Triton X-100 is prepared as Reagent C. The immunoassay is automatically conducted with the following procedures utilized with the automated immunoassay system (sold by Abbott Laboratories, IL under ARCHITECT I2000). In particular, 50 uL of Reagent A and 50 uL of reagent C are mixed with 50 uL of sample. The mixture is incubated at 37° C. for 18 minutes to allow binding of antibody coated on the magnetic microparticles and reactive substance (PIVKA-II) in the sample. Magnetic microparticles are attracted by a magnet and then the residual solutions are removed. The magnetic microparticles are washed by phosphate buffered saline (PBS) so that impurities nonspecifically bound on the magnetic microparticle surface were removed. Fifty uL of Reagent B are then added to the microparticle and then the complex of (antibody coated magnetic microparticle)(PIVKA-II in sample)(acridinium labeled antibody) is formed. After a washing step by PBS, peroxide is added in the alkaline condition, and then acridinium ester produces a luminescent signal which is detected by a photo multiplier tube (PMT).

Following preliminary screening, the PIVKA-II assay protocol (sold under ARCHITECT) as described above was modified to test the ability of various candidate additives to reduce background relative light units (RLU) obtained from serum samples, when each was added in various amounts to the anti-prothrombin conjugate diluent (Reagent B), for use in the second immunoassay reaction. In this study, the anti-PIVKA MAb used in Reagent A was MAb 3C10, and the anti-prothrombin antibody used in the conjugate diluent (Reagent B) was the anti-prothrombin monoclonal antibody MCA1-8 IgG (PI-C163E, IR5.0, 300 ng/mL). Preliminary screening ruled out many proposed substances for reducing background RLU, including casein, fish gelatin, yeast extract and others, though the screening indicated that certain candidates enhanced RLU. Candidate substances subjected to further evaluation were skim milk (milk with cream removed and thus containing less than 1% milk fat), saponin, and (synthetic) sulfobetaine-type zwitterionic detergents including:

3-(N,N-Dimethyloctylammonio)propane-sulfonate (sold under ZWITTERGENT 3-8)

n-Decyl-N,N-dimethyl-3-ammonio-1-propanesulfonate (sold under ZWITTERGENT 3-10)

N-Dodecyl-N,N-dimethyl-3-amino-1-propanesulfonate (sold under ZWITTERGENT 3-12)

n-Tetradecyl-N,N-dimethyl-3-ammonio-1-propanesulfonate (sold under ZWITTERGENT 3-14)

n-Hexadecyl-N,N-dimethyl-3-ammonio-1-propanesulfonate (sold under ZWITTERGENT 3-16)

n-Octadecyl-N,N-dimethyl-3-ammonio-1-propanesulfonate (sold under ZWITTERGENT 3-18 or ANZERGENT 3-18)

"Amidosulfobetaine-14"; 3-[N,N-Dimethyl(3-myristoylaminopropyl)ammonia]propanesulfonate (sold under ZWITTERGENT ASB-14)

"Amidosulfobetaine-16" (sold under ZWITTERGENT ASB-16)

Also evaluated were Lipidure405, BG Solution 2, and C16APS. pH was maintained at 5.5. Candidate substances were added in one or more amounts at 1.0%, 1.25%, 1.67%, 3.00%, or 5.00% of the conjugate diluent, where solid (e.g., powdered) additives were added as % w/v, and liquid additives were added as either % w/v or % v/v. Table 2 summarizes various combinations of additives tested including n-Hexadecyl-N,N-dimethyl-3-ammonio-1-propanesulfonate (sold under ZWITTERGENT 3-16) as the sulfobetaine-type zwitterionic detergent.

Figure 2:
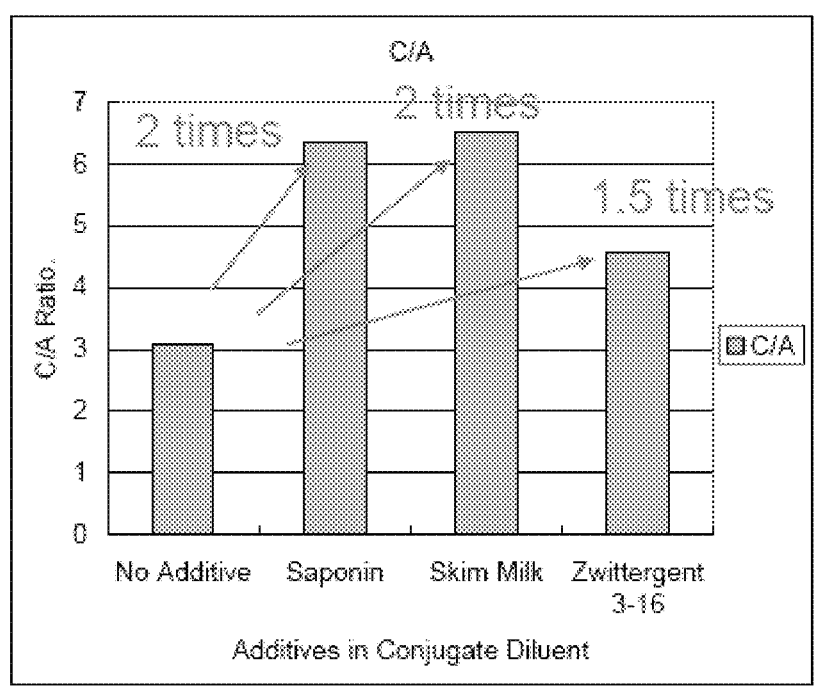
FIG. 2 is a bar graph comparing sensitivity of an immunoassay conducted according to the format of FIG. 1, using a conjugate diluent containing no additive or diluents containing saponin, skim milk or n-Hexadecyl-N,N-dimethyl-3-ammonio-1-propanesulfonate (sold under ZWITTERGENT 3-16) as an additive in the conjugate diluent.
Figure 3:
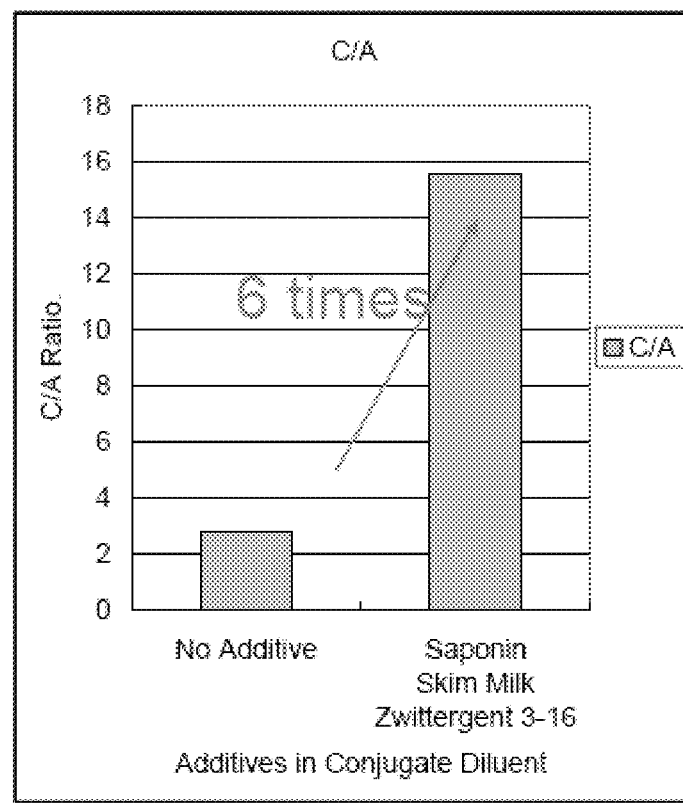
FIG. 3 is bar graph comparing sensitivity of an immunoassay conducted according to the format of FIG. 1, using a conjugate diluent containing no additive or a diluent containing a combination of saponin, skim milk and n-Hexadecyl-N,N-dimethyl-3-ammonio-1-propanesulfonate (sold under ZWITTERGENT 3-16) as additives in the conjugate diluent.

Other sulfobetaine-type zwitterionic detergents were also tested. Results are reported throughout as C/A Ratio. As shown in FIGS. 2 and 3, best results were obtained using the diluents containing saponin, skim milk and n-Hexadecyl-N,N-dimethyl-3-ammonio-1-propanesulfonate (sold under ZWITTERGENT 3-16). FIG. 2 is a bar graph comparing results obtained when the conjugate diluent contained no additive, only saponin, only skim milk, or only n-Hexadecyl-N,N-dimethyl-3-ammonio-1-propanesulfonate (sold under ZWITTERGENT 3-16). FIG. 3 is a bar graph comparing results obtained when the conjugate diluent contained no additive, and when the conjugate diluent contained a combination of skim milk (1.67%), saponin (1.00%), and n-Hexadecyl-N,N-dimethyl-3-ammonio-1-propanesulfonate (sold under ZWITTERGENT 3-16) (1.60%).

Figure 4:
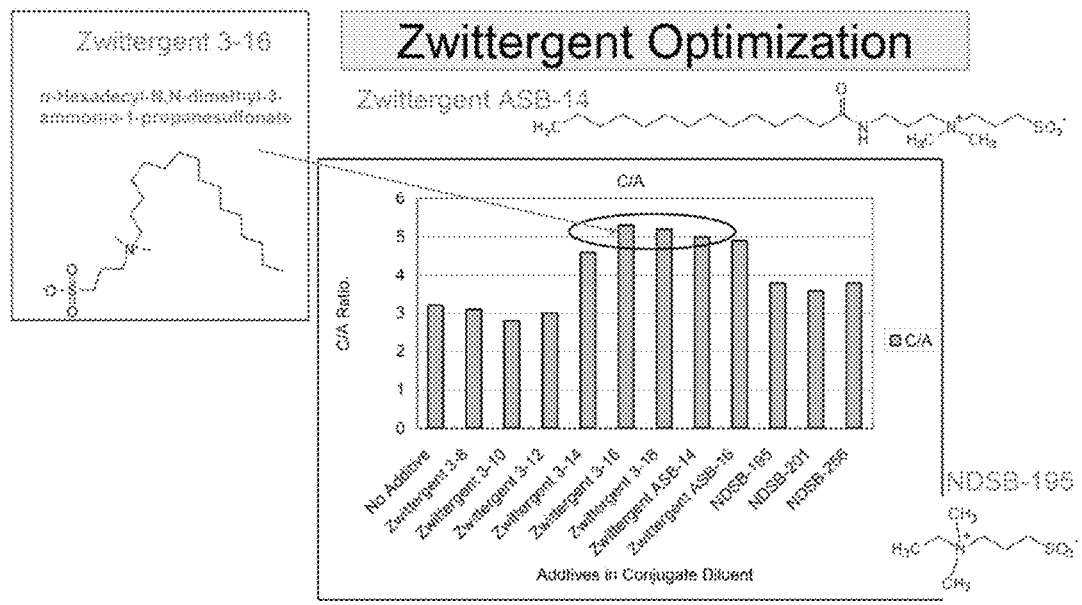
FIG. 4 is a bar graph comparing sensitivity of an immunoassay conducted according to the format of FIG. 1, using a conjugate diluent containing no additive or a diluent containing a combination of saponin, skim milk and one of several sulfobetaine-type zwitterionic detergents tested.

Relative performance of various sulfobetaine-type zwitterionic detergents in the combination of additives was also tested. As shown in FIG. 4, best sensitivity of the assay was obtained n-Hexadecyl-N,N-dimethyl-3-ammonio-1-propanesulfonate (sold under ZWITTERGENT 3-16), but good improvement of sensitivity, over that obtained using no additives, was also obtained using any one of n-Tetradecyl-N,N-dimethyl-3-ammonio-1-propanesulfonate (sold under ZWITTERGENT 3-14), n-Octadecyl-N,N-dimethyl-3-ammonio-1-propanesulfonate (sold under ZWITTERGENT 3-18), Amidosulfobetaine-14 (sold under ZWITTERGENT ASB-14) and Amidosulfobetaine-16 (sold under ZWITTERGENT ASB-16).

Example 2: $Ca^{++}$ Dependency of MCA1-8 Conjugate Diluent

The results obtained from Example 2 as described above suggested that perhaps a certain constituent or constituents of skim milk and saponin are important for improving sensitivity of the MCA1-8 conjugate diluent for detecting PIVKA-II.

The possibility that calcium or magnesium ion might play a role in improving sensitivity was investigated by conducting the PIVKA-II assay protocol (sold under ARCHITECT) as described above, modified by adding certain amounts of $Ca^{++}$ (as $CaCl_2$) or $Mg^{++}$ (as $MgCl_2$) to the conjugate diluent, and conducting the second assay reaction at pH 5.5 and at pH 6.0. Test diluents contained one of the following: No additive, or 30 mM $Ca^{++}$ or 30 mM $Mg^{++}$ as the additive.

TABLE 2

| | ID | Additive 1 | conc. | Additive 2 | conc. | Additive 3 | conc. | Additive 4 | conc. | pH | Lot | | B/A | C/A |
|---|---|---|---|---|---|---|---|---|---|---|---|---|---|---|
| 1 | CD | C NA | | NA | | NA | | NA | | 5.5 | 2567030- | C | 1.3 | 3.2 |
| 2 | CD-AXM | 1 Skim Milk | 1.00% | Saponin | 1.00% | NA | | NA | | 5.5 | 2567034- | 1 | 2.6 | 8.1 |
| 3 | CD-AXM | 2 Skim Milk | 1.00% | NA | | C16APS | 1.60% | NA | | 5.5 | 2567034- | 2 | 2.8 | 9.5 |
| 4 | CD-AXM | 3 Skim Milk | 1.00% | Saponin | 1.00% | C16APS | 1.60% | NA | | 5.5 | 2567034- | 3 | 3.4 | 11.4 |
| 5 | CD-AXM | 4 Skim Milk | 3.00% | Saponin | 1.00% | NA | | NA | | 5.5 | 2567034- | 4 | 2.7 | 9.1 |
| 6 | CD-AXM | 5 Skim Milk | 3.00% | NA | | C16APS | 1.60% | NA | | 5.5 | 2567034- | 5 | 3.1 | 10.9 |
| 7 | CD-AXM | 6 Skim Milk | 1.67% | Saponin | 1.00% | C16APS | 1.60% | NA | | 5.5 | 2567034- | 6 | 3.0 | 11.9 |
| 8 | CD-AXM | 7 NA | | Saponin | 1.00% | C16APS | 1.60% | NA | | 5.5 | 2567034- | 7 | 2.7 | 10.2 |
| 9 | CD-AX | 7 NA | | Saponin | 1.00% | NA | | NA | | 5.5 | 2567030- | 7 | 2.5 | 8.5 |
| 10 | CD-AX | 10 NA | | NA | | C16APS | 1.60% | NA | | 5.5 | 2567030- | 10 | 1.4 | 3.8 |
| 11 | CD-AX | 13 Skim Milk | 1.00% | NA | | NA | | NA | | 5.5 | 2567030- | 13 | 2.0 | 5.7 |
| 12 | CD-AX | 14 Skim Milk | 3.00% | NA | | NA | | NA | | 5.5 | 2567030- | 14 | 2.6 | 8.2 |
| 13 | CD-EX | 1 Skim Milk | 1.25% | Saponin | 1.00% | C16APS | 1.20% | Lipidure405 | 0.63% | 5.5 | 2567034- | 8 | 2.8 | 10.5 |
| 14 | CD-EX | 2 Skim Milk | 1.25% | Saponin | 1.00% | C16APS | 1.20% | LipidureSol.2 | 0.63% | 5.5 | 2567034- | 9 | 3.3 | 11.6 |

Figure 5:
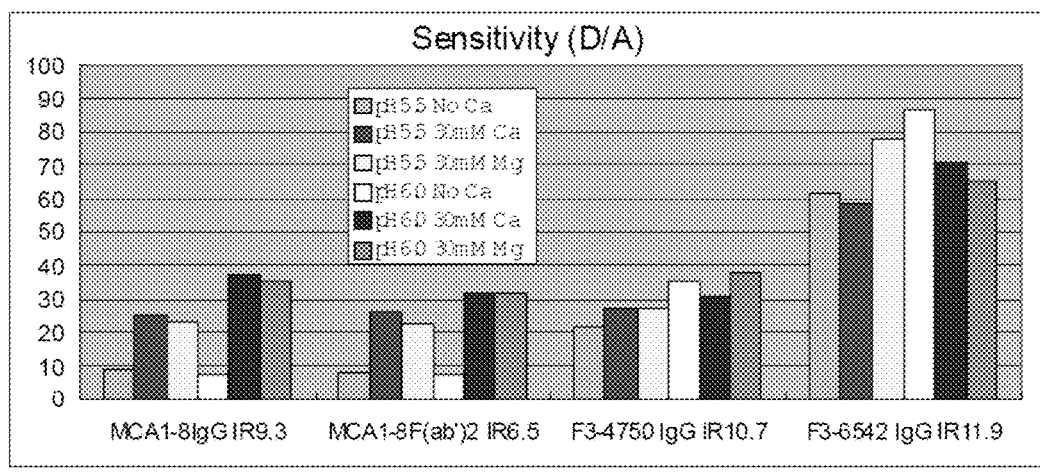
FIG. 5 is a bar graph comparing sensitivity of an immunoassay generally conducted according to the format of FIG. 1 using either MCA1-8 IgG, MCA1-8F(ab')2, F3-4750 IgG, or F3-6542 IgG as the labeled antibody in the conjugate, and a conjugate diluent containing no additive or a diluent containing either 30 mM $CaCl_2$ or 30 mM $MgCl_2$, at pH 5.5 and at pH 6.0.

The results are summarized in Table 3 below, and the bar graph shown in FIG. 5, showing that at pH 5.5 and at pH 6.0, a conjugate diluent containing either 30 mM $Ca^{++}$ or 30 mM $Mg^{++}$ displays improved sensitivity over that obtained using a conjugate diluent containing no additive.

TABLE 3

| | Sensitivity (D/A) | | | | | |
|---|---|---|---|---|---|---|
| | Cal-A: 0 mAU/mL pH 5.5 | | | Cal-D: 100 mAU/mL (= previous CalC) pH 6.0 | | |
| | No Ca | 30 mM Ca | 30 mM Mg | No Ca | 30 mM Ca | 30 mM Mg |
| MCA1-8IgG IR9.3 | 8.7 | 25.3 | 23.1 | 7.5 | 37.0 | 35.1 |
| MCA1-8F(ab')2 IR6.5 | 7.7 | 25.9 | 22.4 | 7.1 | 32.0 | 32.1 |
| F3-4750 IgG IR10.7 | 21.6 | 27.2 | 27.2 | 35.1 | 30.9 | 37.7 |
| F3-6542 IgG IR11.9 | 61.7 | 59.0 | 77.7 | 86.1 | 70.5 | 65.4 |

Figure 6:
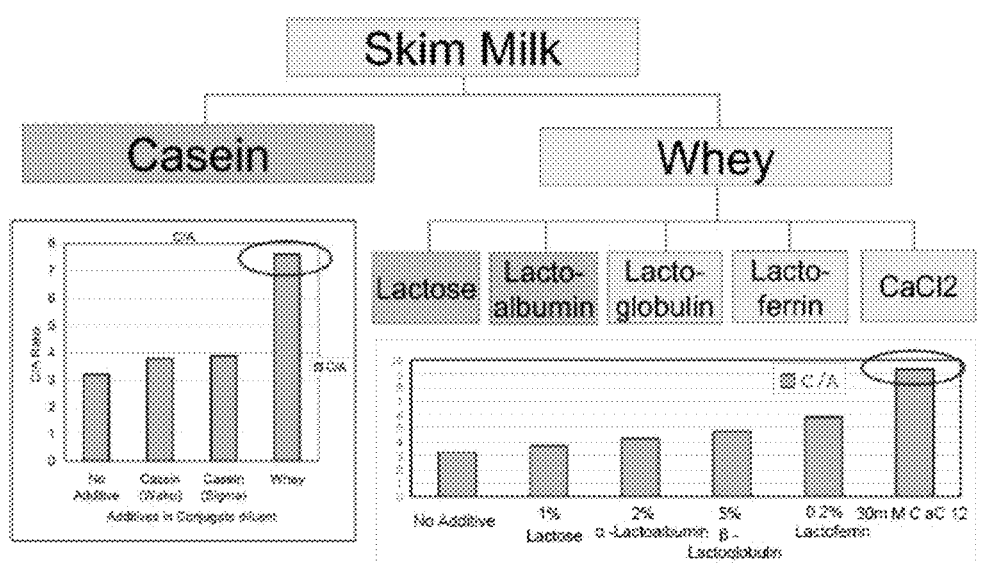
FIG. 6 is a schematic diagram including two bar graphs comparing sensitivity of an immunoassay conducted according to the format of FIG. 1, using either MCA1-8 IgG or MCA1-8F(ab')2 as the labeled antibody in the conjugate, when conjugate diluents containing one of various constituents of skim milk as an additive to the conjugate diluent.

The contribution of various known components of skim milk were also investigated by conducting the modified PIVKA-II assay protocol (sold under ARCHITECT) as described above, substituting for skim milk any one of several of its various components in the exemplary combination of diluent additives as described above: skim milk (1.67%), saponin (1.00%), and n-Hexadecyl-N,N-dimethyl-3-ammonio-1-propanesulfonate (sold under ZWITTERGENT 3-16) (1.60%). As shown in FIG. 6, casein, whey, and constituents of whey (lactose, lactalbumin, lactoglobulin, lactoferrin, and $CaCl_2$) were tested as substitutes for skim milk, using 1.67% of casein (from each of two different sources as indicated, Wako and Sigma-Aldrich Co.), 1.67% whey, 1% lactose, 2% α-lactalbumin, 5% β-lactoglobulin, 0.2% lactoferrin, or 30 mM $CaCl_2$. As shown at left in FIG. 6, sensitivity was improved over a conjugate diluent containing no additive only when whey, and not casein, was substituted for skim milk as an additive in the diluent. As shown at right in FIG. 6, among the constituents of whey, best sensitivity was obtained when the conjugate diluent contained 30 mM $CaCl_2$.

Figure 7:
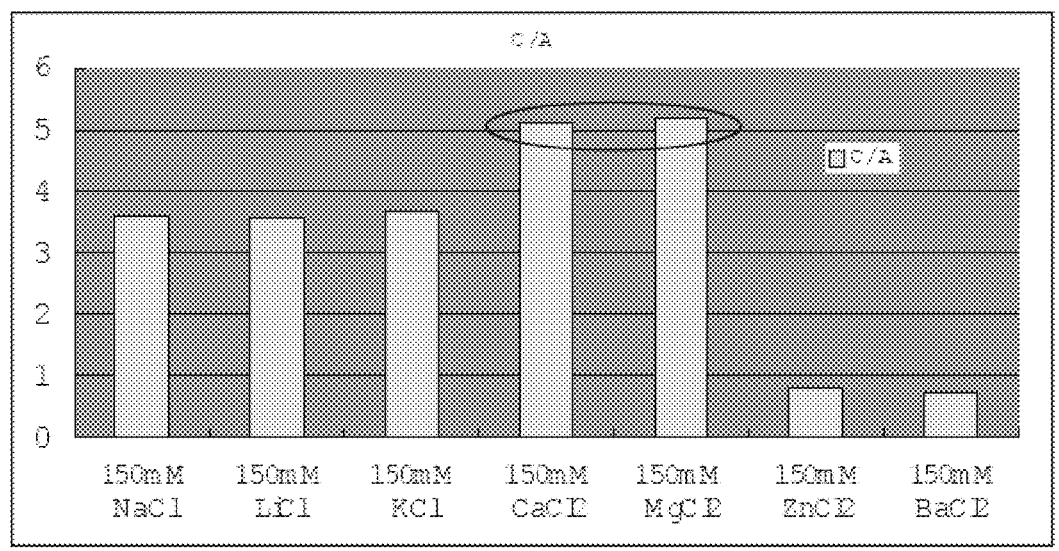
FIG. 7 is a bar graph comparing sensitivity of an immunoassay conducted according to the format of FIG. 1, using a conjugate diluent containing 150 mM of one of seven metal chloride salts.

The possibility that metal chloride salts other than $CaCl_2$ or $MgCl_2$ might improve sensitivity of the conjugate diluent was also tested substantially as described above, using a conjugate diluent containing 150 mM of one of: NaCl, LiCl, KCl, $CaCl_2$, $MgCl_2$, $ZnCl_2$ or $BaCl_2$, as summarized in Table 4 below, and shown in FIG. 7. The results show that best sensitivity is obtained with a diluent containing 150 mM of $CaCl_2$ or $MgCl_2$.

TABLE 4

| | Conjugate Inf. | Best Diluent (Saponin, Milk, Zw3-16) | 150 mM NaCl | 150 mM LiCl | 150 mM KCl | 150 mM CaCl2 | 150 mM MgCl2 | 150 mM ZnCl2 | 150 mM BaCl2 |
|---|---|---|---|---|---|---|---|---|---|
| PI-C2-A | 0 mAU/mL | 329 | 885 | 807 | 946 | 224 | 256 | 1597 | 24627 |
| PI-C2-B | 20 mAU/mL | 1160 | 1361 | 1214 | 1346 | 412 | 436 | 1795 | 22946 |
| PI-C2-C | 100 mAU/mL | 3956 | 3196 | 2877 | 3460 | 1146 | 1329 | 1244 | 18338 |
| | B/A | 3.5 | 1.5 | 1.5 | 1.4 | 1.8 | 1.7 | 1.1 | 0.9 |
| | C/A | 12.0 | 3.6 | 3.6 | 3.7 | 5.1 | 5.2 | 0.8 | 0.7 |

One skilled in the art would readily appreciate that the methods and kits described in the present disclosure are well adapted to carry out the objects and obtain the ends and advantages mentioned, as well as those inherent therein. The methods, procedures, treatments, molecules, specific compounds and kits described herein are merely representative and exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A method for measuring Protein Induced by Vitamin K Absence or Antagonist-II (PIVKA-II) in a test sample, the method comprising:
    (a) contacting the test sample with a first reagent, wherein the first reagent consists of a solid phase coated with an anti-PIVKA-II antibody, a buffer, a detergent, and bovine serum albumin, wherein the anti-PIVKA-II antibody binds to an epitope on PIVKA-II to form an anti-PIVKA-II antibody-PIVKA-II antigen complex in the presence of the buffer, the detergent, and the bovine serum albumin;
    (b) contacting the anti-PIVKA-II antibody-PIVKA-II antigen complex with a second reagent, wherein the second reagent comprises a detectably-labeled anti-prothrombin antibody, 2-(N-morpholino)ethanesulfonic acid (MES) buffer with a bovine protein stabilizer, an antimicrobial agent, and 30 mM-200 mM magnesium chloride ($MgCl_2$), wherein the anti-prothrombin antibody is MCA1-8, binds to an epitope on PIVKA-II, and forms an anti-PIVKA-II antibody-PIVKA-II antigen-anti-prothrombin antibody complex; and
    (c) determining the PIVKA-II concentration in the test sample based on the signal generated by the detectable label in the anti-PIVKA-II antibody-PIVKA-II antigen-anti-prothrombin antibody complex formed in (b).

2. The method of claim 1, wherein the method is carried out in an automated measuring apparatus.

* * * * *